(12) United States Patent
Burdick

(10) Patent No.: US 6,468,201 B1
(45) Date of Patent: Oct. 22, 2002

(54) APPARATUS USING PNP BIPOLAR TRANSISTOR AS BUFFER TO DRIVE VIDEO SIGNAL

(75) Inventor: Kenneth J. Burdick, Skaneateles, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 29 days.

(21) Appl. No.: 09/844,231

(22) Filed: Apr. 27, 2001

(51) Int. Cl.[7] .............................. A61B 1/04; H04N 7/18
(52) U.S. Cl. ........................................ 600/109; 348/76
(58) Field of Search .................................. 600/101, 109, 600/110; 348/65, 74, 76, 294, 300

(56) References Cited

U.S. PATENT DOCUMENTS

| | | | | |
|---|---|---|---|---|
| 4,354,749 A | | 10/1982 | Hosoda | |
| 4,516,153 A | * | 5/1985 | Krull et al. | 348/665 |
| 4,868,646 A | | 9/1989 | Tsuji | |
| 4,979,035 A | | 12/1990 | Uehara et al. | |
| 5,023,570 A | * | 6/1991 | Matsumoto | 327/310 |
| 5,278,656 A | | 1/1994 | Hynecek et al. | |
| 5,291,151 A | * | 3/1994 | Fujiwara et al. | 330/282 |
| 5,946,034 A | * | 8/1999 | Cortiula | 348/315 |
| 6,084,461 A | * | 7/2000 | Colbeth et al. | 327/362 |

* cited by examiner

*Primary Examiner*—John P. Leubecker
(74) *Attorney, Agent, or Firm*—Wall Marjama & Bilinski LLP

(57) ABSTRACT

A PNP bipolar transistor or an enhancement mode P-channel FET is used as a buffer to drive a video signal from an imager to video processing circuits. An endoscope with a solid state imager having a negative-going video pulse is used, with a video buffer located at or near the distal end to buffer the CCD video signal. The buffer employs a PNP bipolar transistor that is biased by a bias circuit for the base and a power supply for the collector, both located near the transistor, and a load for the emitter located at some distance from the transistor.

9 Claims, 3 Drawing Sheets

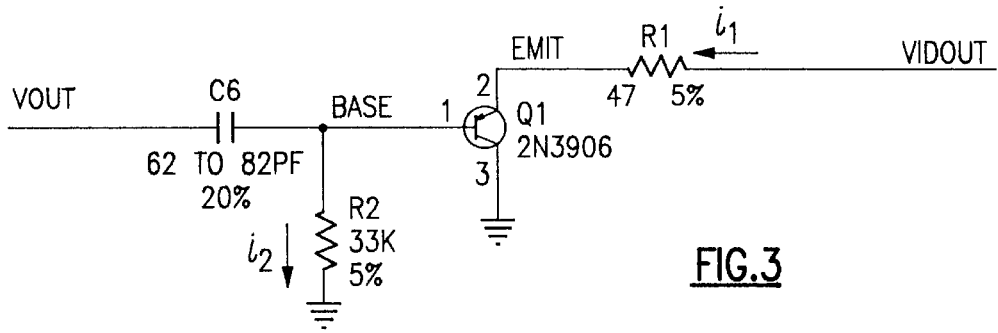
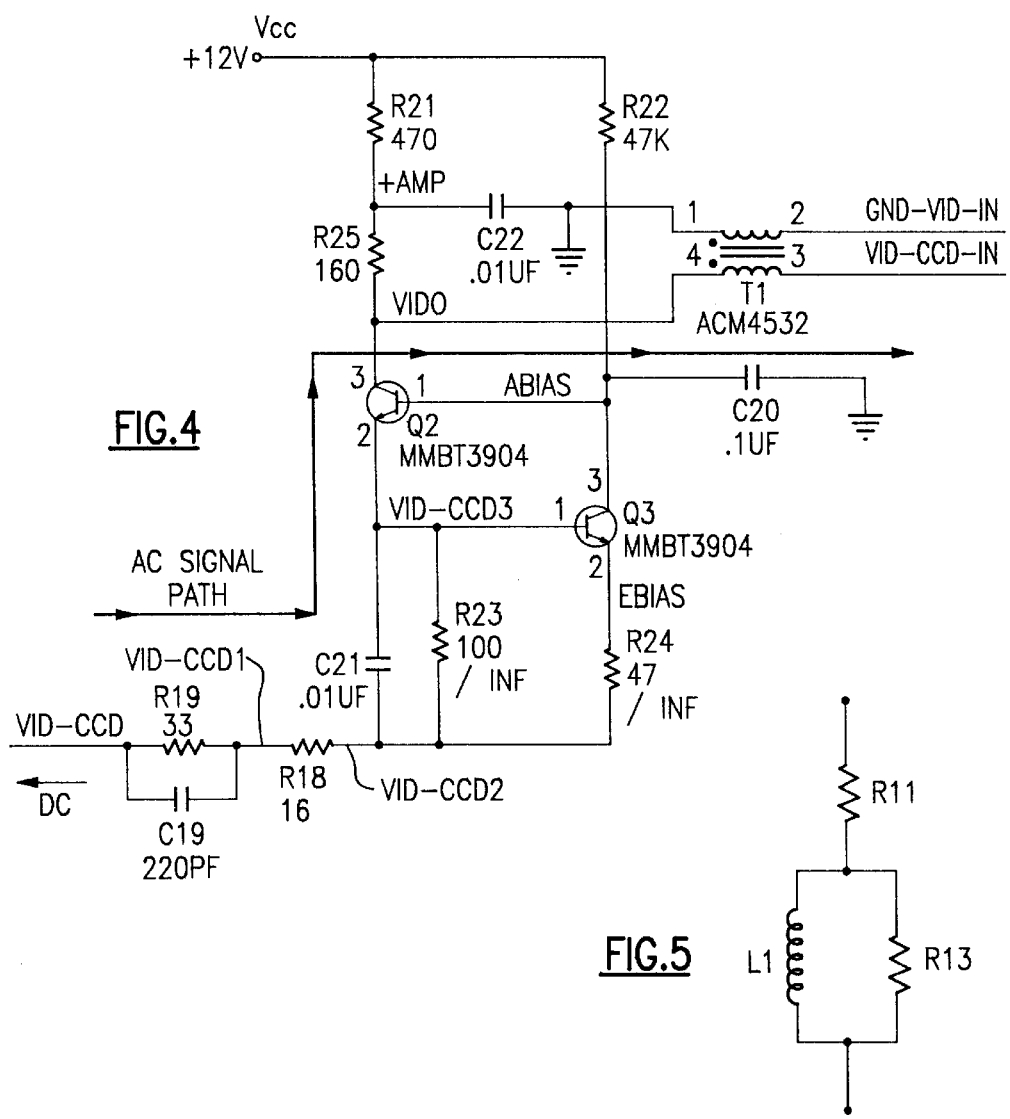

APPARATUS USING PNP BIPOLAR TRANSISTOR AS BUFFER TO DRIVE VIDEO SIGNAL

FIELD OF THE INVENTION

The invention pertains to driving video signals from an imager to video processing circuits, and in particular, to using a PNP transistor as a buffer to drive the signals.

BACKGROUND OF THE INVENTION

High resolution borescopes need to produce the best video picture possible while maintaining the smallest possible size for the imager head assembly. In addition, the smallest amount of power possible must be dissipated in the imager head assembly.

The use of emitter followers and source followers to drive cables is well known and broadly used in practice. NPN emitter followers have been used to drive video cables from CCD imagers. N-channel JFET source followers and video-speed OP AMPS have also been used for this function. The output characteristic of the CCD imager makes it natural to select these types of devices because its DC output voltage provides the correct bias point for them without the addition of any parts.

What is not generally understood is the benefit of using a P-channel FET source follower or especially a PNP emitter follower in this application. The problem of establishing the bias point for these devices contraindicates their use. However, they have characteristics that are useful when the unique signal dynamics of the CCD video signal are considered.

U.S. Pat. No. 4,868,646 (Tsuji) discloses an image pickup apparatus for an electronic endoscope. The pickup unit comprises a solid-state image sensor and a drive generator circuit disposed adjacent to the image sensor for generating drive voltages and having a device for adjusting the amplitude of the drive voltage required to properly drive the solid-state image sensor. Although Tsuji describes an NPN transistor circuit, Tsuji discloses that a PNP transistor can be used with the resistors arranged on the pull-up side. However, Tsuji just generates reference voltages in the head to reduce the number of wires and doesn't have anything to do with the signal out.

U.S. Pat. No. 5,278,656 (Hynecek et al.) discloses an image system comprising a solid-state imaging device, a buffer means provided in the vicinity of the imaging device, and a signal transmitting cable transmitting the signal amplified in the current by the buffer means to the signal processing means side to produce high picture quality. Hynecek discloses good prior art in FIGS. 3, 4, 14, and 15 for reducing power, which is an aspect of the present invention.

U.S. Pat. No. 4,979,035 (Uehara et al.) discloses an electronic endoscope with a CCD output circuit of positive polarity.

U.S. Pat. No. 4,354,749 (Hosoda) discloses an endoscope apparatus of general interest.

SUMMARY OF THE INVENTION

Briefly stated, a PNP bipolar transistor or an enhancement mode P-channel FET is used as a buffer to drive a video signal from an imager to video processing circuits. An endoscope with a solid state imager having a negative-going video pulse is used, with a video buffer located at or near the distal end to buffer the CCD video signal. The buffer employs a PNP bipolar transistor that is biased by a bias circuit for the base and a power supply for the collector, both located near the transistor, and a load for the emitter located at some distance from the transistor.

According to an embodiment of the invention, an endoscope apparatus includes a solid state imager having a negative-going video pulse and a video buffer located substantially at a distal end of the apparatus to buffer a video signal produced by the solid state imager. The video buffer includes a PNP bipolar transistor biased by a base bias circuit connected to a base of the transistor and a power supply connected to a collector of the transistor. The base bias circuit and the power supply are located in the distal end of the apparatus; and an emitter of the transistor is connected through a cable to a load for the emitter, where the load is located substantially at a proximal end of the apparatus.

BRIEF DESCRIPTION OF THE DRAWINGS

FIG. 3 shows a schematic of a buffer to drive the video signal from the imager to video processing circuits according to an embodiment of the invention.

FIG. 4 shows a schematic of a load and amplifier circuit which receives the video signal from a cable connected to the circuit of FIG. 3.

FIG. 5 shows an optional cable compensation circuit which is used in a variation of the circuit of FIG. 4.

DETAILED DESCRIPTION OF THE PREFERRED EMBODIMENT

Figure 1:
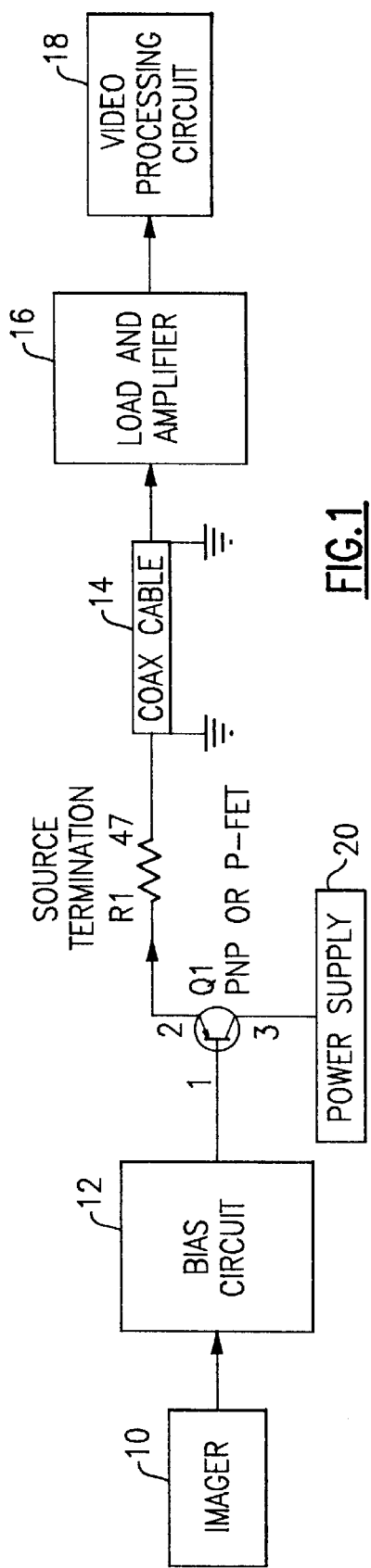
FIG. 1 shows a block diagram of an embodiment of the present invention.

Referring to FIG. 1, the basic idea of the invention is the use of a PNP bipolar transistor Q1 or enhancement mode P-channel FET (not shown) as the buffer to drive a video signal from an imager 10, such as a CCD or CMOS imager, to a video processing circuit 18. The signal is transmitted from imager 10 through a bias circuit 12 to a base 1 of transistor Q1. A power supply 20 biases Q1 at a collector 3. A source termination R1 is in series between an emitter 2 of transistor Q1 and a coaxial cable 14. The signal passes through a load and amplifier 16 before entering video processing circuit 18. The bias circuit 12, power supply 20, and load are required for any configuration, PNP or otherwise. The amplifier is optional in any configuration, but may improve system performance.

Figure 2:
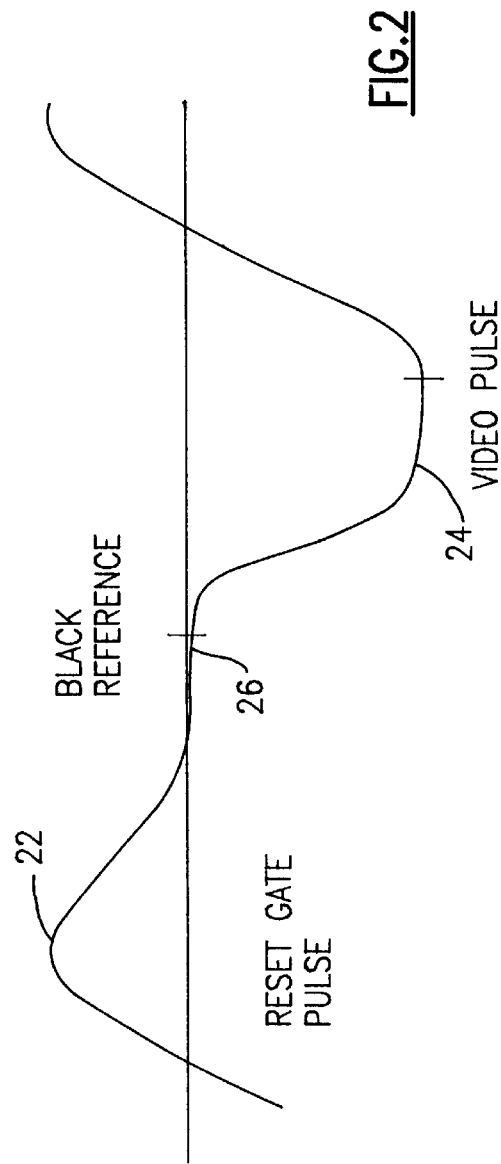
FIG. 2 shows a waveform of a video signal waveform from an imager.

Referring also to FIG. 2, the video signal from imager 10 is shown. The signal is composed of two pulses, a reset gate pulse 22 which contains no useful information, and a video pulse 24 that represents the brightness of light shining on a pixel in the imager. The video signal has a large random noise component added to it by the imager output circuitry that can degrade the picture quality. In practice, the signal is sampled by video processing circuit 18 at two places, in a black reference 26 and in video pulse 24 (marked with the crosses in FIG. 2) to determine the amplitude of the video pulse, which sampling greatly reduces the random noise.

Reset gate pulse 22 contains additional noise, both random noise and noise caused by digital video processing circuitry 18. To the extent that reset gate pulse 22 is included in the two samples, it causes noise effects in the picture. Thus, if we move the black reference 26 sample earlier or the video pulse 24 sample later (i.e., into the reset gate pulse), it harms the image. Likewise, spreading of the reset gate into the sample intervals harms the image.

Emitter followers and source followers have the property that they are able to drive signals of one polarity better than signals of the opposite polarity. The NPN bipolar and N-FET types drive positive going signals better than negative going ones. For the CCD video signal, they reproduce the reset gate pulse 22 well, but have difficulty reproducing large video pulse 24 signals. The signal handling limit occurs when the current driven into the cable (Vsignal/2*Zcable) approaches or exceeds the DC current through the transistor (Iemitter). For the PNP transistor or P-FET, the opposite is true, so if any limiting occurs, it only serves to reduce the amplitude of reset gate pulse 22, resulting in a net benefit.

A DC current must be maintained through transistor Q1 in order to control the output impedance of the buffer. This current is supplied by load circuit 16 at the end of cable 14. Bias circuit 12 and power supply 20 must be chosen so that an uncorrupted signal is delivered without causing excess power dissipation in the imager head, and must also be free of noise that would degrade the quality of the picture. The voltage from base 1 to collector 3 (Vbc) must be large enough for linear operation, while the voltage from emitter 2 to collector 3 (Vce) must be kept low to limit power. Vbc of about 1 to 2 volts is optimum for typical CCD imagers.

A typical CCD requires two power supplies which may be used to provide bias and power supply voltages: Vh with a voltage of about +15 volts, and Vl at around −7.5 to −8.5 volts. Some CCD products have a clock buffer supply Vclk at about+5 volts that may also be employed.

Referring to FIG. 3, an embodiment of the invention is shown in which collector 3 is connected to a reference potential. Base 1 is connected to the reference potential via a resistor R2, and is connected to bias circuit 12 via a coupling capacitor C6. The key to this embodiment is to control the current. Current $i_1$ sets current $i_2$ which sets the DC operating voltage (DC bias point). We need enough voltage on collector 3 compared to base 1 so that transistor Q1 doesn't go non-linear.

Referring to FIG. 4, load and amplifier circuit 16 is shown in detail. The purpose of this circuit is to get the HF AC signal from the circuit of FIG. 3 out to video processing circuit 18 (FIG. 1), which is preferably a DSP. The AC signal enters a cable termination impedance portion which consists of a resistor R19 in parallel with a capacitor C19. The preferred impedance depends on the cable length and type. The purpose of the cable termination impedance is to create a 50 ohm impedance and boost the HF components of the AC signal relative to the LF components.

A transistor Q3 controls the current through a transistor Q2. Resistors R23 and R24 determine the current through Q3. The B–E voltage through transistor Q3 along with resistors R23 and R24 control the current through transistor Q2, which is the current to the image head in imager 10 (FIG. 1). That is, transistor Q3 determines and transistor Q2 provides the DC current to the image head. Transistor Q2 is used as a common-base amplifier in which the base is connected to the reference potential at high frequencies via a capacitor C20. At low frequencies, the base moves to control the current. A capacitor C21 is a coupling capacitor. A resistor R21 and a capacitor C22 filter the signal to clean up noise imposed by the power supply (Vcc). A common-mode transformer T1 is used because this circuit and the DSP are on different circuit boards. The output voltage of the AC signal is developed across a resistor R25.

Referring to FIG. 5, resistor R25 is optionally replaced with an additional cable compensation circuit with a resistor R11 in series with a parallel combination of an inductor L1 and a resistor R13. The circuit boosts the high frequencies (HF) relative to the low frequencies (LF).

Figure 6A:
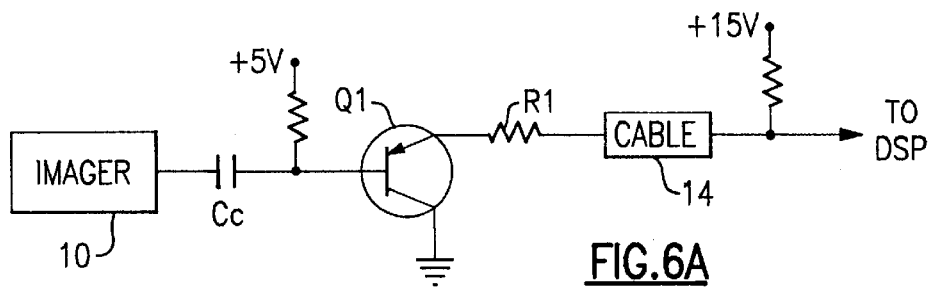
FIG. 6A shows an alternative embodiment of the circuit of FIG. 3.
Figure 6B:
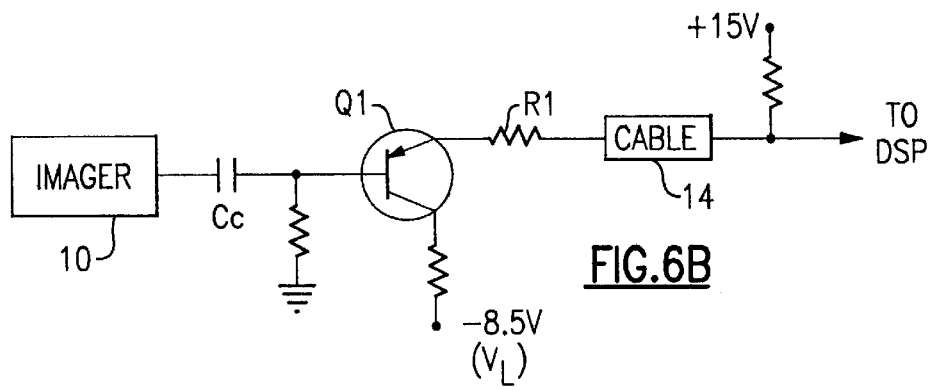
FIG. 6B shows an alternative embodiment of the circuit of FIG. 3.
Figure 6C:
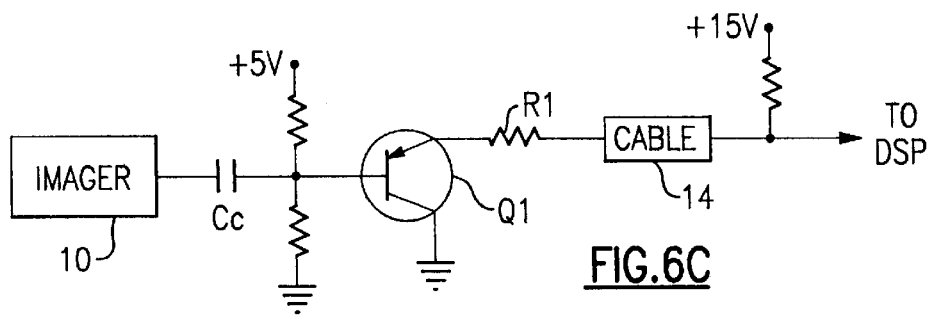
FIG. 6C shows an alternative embodiment of the circuit of FIG. 3.
Figure 6D:
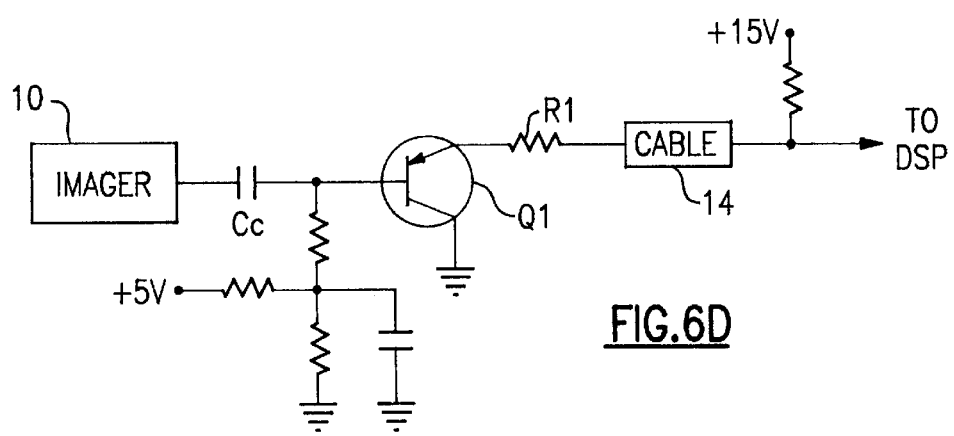
FIG. 6D shows an alternative embodiment of the circuit of FIG. 3.

Referring to FIGS. 6A–6D, alternative embodiments of the invention are shown. In FIG. 6A, the circuit has the ability to drive hard on negative outputs corresponding to the video signal. Although there is low power dissipation, noise comes in from the 5 volt power supply. In FIG. 6B, there is more power dissipated, but very little power noise. In FIG. 6C, there is less power dissipated, but there is still about ½ of the 5 volt power supply noise. In FIG. 6D, there is good power and good noise, but a separate power supply is still used to bias transistor Q1. The embodiment of FIG. 3 is preferred because no power supply noise is introduced.

While the present invention has been described with reference to a particular preferred embodiment and the accompanying drawings, it will be understood by those skilled in the art that the invention is not limited to the preferred embodiment and that various modifications and the like could be made thereto without departing from the scope of the invention as defined in the following claims.

What is claimed is:

1. An endoscope apparatus which includes a solid state imager having a negative-going video pulse, comprising:
   a video buffer located substantially at a distal end of said apparatus to buffer a video signal produced by said solid state imager;
   said video buffer including a PNP bipolar transistor biased by a base bias circuit connected to a base of said transistor and a power supply connected to a collector of said transistor, wherein said base bias circuit and said power supply are located in said distal end of said apparatus; and
   an emitter of said transistor connected through a cable to a load for said emitter, said load being located substantially at a proximal end of said apparatus.

2. An endoscope apparatus according to claim 1, further comprising a source termination resistor connected in series between said transistor and said cable.

3. An endoscope apparatus according to claim 2, wherein said base bias circuit includes a resistor connected to ground and a capacitor coupling said solid state imager to said base.

4. An endoscope apparatus according to claim 3, wherein said power supply for said collector is ground or derived directly from ground, and wherein a proper operating point for said transistor is set by controlling current supplied by said emitter load and setting a value of said resistor in said base bias circuit according to a gain of said transistor and said emitter load current.

5. An apparatus according to claim 3, wherein said power supply for said collector is derived from a power supply to said solid state imager.

6. An endoscope apparatus according to claim 1, wherein said base bias circuit includes a resistor connected to ground and a capacitor coupling said solid state imager to said base.

7. An endoscope apparatus according to claim 6, wherein said power supply for said collector is ground or derived directly from ground, and wherein a proper operating point for said transistor is set by controlling current supplied by said emitter load and setting a value of said resistor in said base bias circuit according to a gain of said transistor and said emitter load current.

8. An apparatus according to claim 7 wherein said load is a cascode amplifier configured to supply a constant current to said emitter.

9. An apparatus according to claim 8, wherein said cascode amplifier includes:

- a second transistor whose emitter is connected to said emitter of said PNP bipolar junction transistor via a second coupling capacitor;
- a third transistor whose collector is directly connected to a base of said second transistor and to a third capacitor which is connected to ground, and a base of said third transistor is directly connected to said emitter of said second transistor;
- a second resistor in parallel across said second coupling capacitor from a first side of said second coupling capacitor to a second side of said second coupling capacitor; and
- a third resistor connected directly on one end to an emitter of said third transistor and on another end to said second side of said coupling capacitor,
- wherein a base-emitter voltage of said third transistor along with said second and third resistors control a current through said second transistor.

* * * * *